United States Patent
Schindelholz et al.

(10) Patent No.: US 9,927,381 B2
(45) Date of Patent: Mar. 27, 2018

(54) APPARATUS, SYSTEMS AND METHODS FOR LOCAL IN SITU MEASUREMENT OF CORROSION CONDITION INFORMATION WITH CONTACTLESS ELECTRODES

(71) Applicant: LUNA INNOVATIONS INCORPORATED, Roanoke, VA (US)

(72) Inventors: Mara Elizabeth Schindelholz, Roanoke, VA (US); Fritz John Friedersdorf, Roanoke, VA (US); Nathan Kelly Brown, Roanoke, VA (US); Jeffrey Coleman Demo, Roanoke, VA (US); Conrad Koeing Andrews, Roanoke, VA (US); Paul Gordon Muskopf, Roanoke, VA (US)

(73) Assignee: Luna Innovations Incorporated, Roanoke, VA (US)

(*) Notice: Subject to any disclaimer, the term of this patent is extended or adjusted under 35 U.S.C. 154(b) by 116 days.

(21) Appl. No.: 14/746,144

(22) Filed: Jun. 22, 2015

(65) Prior Publication Data
US 2015/0377814 A1     Dec. 31, 2015

Related U.S. Application Data

(60) Provisional application No. 62/015,750, filed on Jun. 23, 2014.

(51) Int. Cl.
*G01N 27/20* (2006.01)
*G01N 27/02* (2006.01)

(52) U.S. Cl.
CPC ................ *G01N 27/026* (2013.01)

(58) Field of Classification Search
CPC ...... G01N 27/026; G01N 27/20; G01N 27/06; G01N 27/02; G01N 27/041; G01N 27/04; G01R 27/02
See application file for complete search history.

(56) References Cited

U.S. PATENT DOCUMENTS

| | | |
|---|---|---|
| 5,859,537 A | 1/1999 | Davis et al. |
| 6,911,828 B1 * | 6/2005 | Brossia .............. G01N 17/02 324/649 |

(Continued)

OTHER PUBLICATIONS

K.N. Allahar et al, "Non-substrate EIS monitoring of organic coatings with embedded electrodes" Progress in Organic Coatings, 67, 2, Feb. 2010, pp. 180-187.

(Continued)

*Primary Examiner* — Jermele M Hollington
*Assistant Examiner* — Suresh K Rajaputra
(74) *Attorney, Agent, or Firm* — Nixon & Vanderhye P.C.

(57) ABSTRACT

A sensing device includes a pair of contactless electrodes for placement on a coating on a surface of a structure or within or between one or more coatings on or over the surface of the structure. The electrodes function as sensors when activated to generate a current flow through the electrodes at multiple different frequencies. The sensing device also includes contactless control circuitry co-located with or separate from the electrodes that transmits impedance data generated from the activated electrodes. The impedance data is associated with corrosion condition information of the structure and/or the one or more coatings. A data collection system and display system useable with the sensing device are also described.

28 Claims, 9 Drawing Sheets

(56) References Cited

U.S. PATENT DOCUMENTS

| | | | |
|---|---|---|---|
| 7,477,060 B2 | 1/2009 | Yu et al. | |
| 7,558,701 B2* | 7/2009 | Andarawis | G01M 5/00 |
| | | | 702/183 |
| 7,675,295 B2 | 3/2010 | Materer et al. | |
| 7,877,009 B2 | 1/2011 | Wang et al. | |
| 8,085,165 B2 | 12/2011 | Wavering et al. | |
| 2008/0238449 A1* | 10/2008 | Shizu | G01N 27/226 |
| | | | 324/689 |
| 2009/0058427 A1* | 3/2009 | Materer | G01N 17/04 |
| | | | 324/649 |
| 2010/0039127 A1* | 2/2010 | Orazem | C23F 13/04 |
| | | | 324/718 |
| 2012/0081136 A1 | 4/2012 | Davis et al. | |

OTHER PUBLICATIONS

C. Andrade et al, "Feasibility of determining corrosion rates by means of stray current-induced polarization" Journal of Applied Electrochemistry, vol. 38, Issue 10, May 2005, pp. 1467-1476.

A. Nogueira et al, "On the possibility of using embedded electrodes for the measurement of dielectric properties in organic coatings" Progress in Organic Coatings, 59, 3, Jun. 2007, pp. 186-191.

* cited by examiner

APPARATUS, SYSTEMS AND METHODS FOR LOCAL IN SITU MEASUREMENT OF CORROSION CONDITION INFORMATION WITH CONTACTLESS ELECTRODES

PRIORITY APPLICATION

This application claims priority from U.S. provisional patent application 62/015,750, filed on Jun. 23, 2014, the contents of which are incorporated herein by reference.

GOVERNMENT RIGHTS

This invention was made with Government support under Contract Nos. N00014-12-C-0420 and N00014-14-C-0040 awarded by the Department of the Navy. The Government has certain rights to the invention.

INTRODUCTION

The example embodiments described below relate to systems and methods for automatically detecting corrosion and coating degradation of coated metallic structures or components. A non-limiting example component is a ship propulsion shaft, with a composite covering and coating, that can be expected to be operated in corrosive environments, e.g., in marine environments.

BACKGROUND AND SUMMARY

The annual cost of corrosion for the U.S. was estimated to be $276 billion or approximately 3.1% of the U.S. Gross Domestic Product. Besides these costs, corrosion also adversely impacts safety and efficiency in a number of economic sectors such as transportation and infrastructure. Aging infrastructure has been deemed "one of the most serious problems faced by society today," in a study performed by the Federal Highway Administration (FHWA). As aging infrastructure and transportation vehicles approach the end of their design lifetime, proper asset management is increasingly important in an effort to safely extend service lifetimes. However, due to the complex nature of these structures, corrosion often occurs in areas that are difficult to access, making regular maintenance checks impossible. Therefore, corrosion maintenance practices are schedule-based, where the extent of material and corrosion damage is examined after a certain number of hours or set calendar service periods. The removal of material to determine the degree of material degradation and corrosion damage is costly and destructive, and although some inspections reveal significant damage, other inspections uncover no damage, which indicates the structure or component had significant remaining service life.

Increasingly, there is a need to transition from these current schedule-based maintenance practices to condition-based practices, where damage is addressed once it reaches a critical level and before a potentially disabling event occurs. Monitoring systems and models predicting future damage have been developed and installed across platforms for corrosion control. In applications where the structural alloys or substrates are difficult to access (structures with multilayer coating and coverings, insulation, or embedded in concrete), however, online monitoring systems are still challenging to implement. For many known monitoring systems, a direct electrical connection to the structure is necessary for performing electrochemical measurements, such as linear polarization or electrochemical impedance spectroscopy, to determine the progression of material degradation and corrosion. This direct electrical connection must be attached to the structure as it is built or it can be added in later. Direct electrical connection between the sensing elements and structure may require penetrations through protective coatings that can then become failure points or otherwise impair the functionality of the protection system. In many applications where the structure is difficult to access, electrically connecting directly to the substrate is impossible due to the possibility of electrical interference or wires through surrounding material becoming failure points.

The use of wireless power and signal transfer to excite the corrosion and coating condition sensors eliminates the need for conductors or physical connectors that penetrate through the coatings, covers, or insulation layers or the structure. Elimination of wired power and communications interfaces also eliminates discontinuities that may become failure points or otherwise impair the functionality of the protective coverings. Finally, wireless power and communications are useful for monitoring moving parts and components such as a propulsion shaft for a ship.

Electrochemical techniques including linear polarization or electrochemical impedance spectroscopy may be used in some monitoring systems for detecting corrosion and coating condition. These techniques can be used to track with time the evolution of barrier properties of coatings and polarization resistance of the metallic structure, which is then converted to a corrosion rate. When these techniques are performed with a two-electrode or three-electrode setup (working, counter, and reference electrode), a direct electrical connection to the structure is required. For a structure that is difficult to access, such as buried in concrete or soil, if the connection was not placed when it was first constructed, it can be extremely costly and difficult to later retrofit an electrical connection to the buried structure. In many cases, it can be impossible to electrically connect to the structure because of the possibility of interference with normal operations of the structure and damage to the coatings, covers, or insulation surrounding it.

Electrochemical measurement techniques also require physical electrical connections between the sensing elements and the power and communications interface. The requirement for physical electrical connections means that batteries or line-power must be available or incorporated in the design. The size of the electronics, batteries, or wiring required for these connections creates difficulties for installing and maintaining embedded systems. In the case of battery powered monitoring systems, battery replacement becomes a routine maintenance burden. For line-powered systems the electrical connection needs to be routed to a power source, and the connections to the embedded sensors need to penetrate through the structure, coatings, covering, or insulation. For moving components these techniques may be impossible or require complex connections, e.g., a slip ring connection, that also introduce complexity, reduce reliability, and increase maintenance activities.

Other nondestructive techniques to monitor a buried structure or a free-standing coated structure and detect both material degradation surrounding the structure and corrosion of the structure itself include acoustic emission, ultrasonic, electromagnetic, thermographic, optical fiber, or radiographic methods. Although these techniques might be effective in detecting corrosion damage over a wide area, they can only detect damage that is on the size order of large pits or cracks and that often has already reached a critical level. The early stages of corrosion that include the breakdown of the passive oxide layer and initiation of corrosion are not detectable using these techniques. They can also be useful for detecting coating degradation but are unable to distinguish degradation between layers in a multilayer coating stack-up.

"Coupons" that are made from the same material as the structure may be buried or placed near the structure of interest in combination with a monitoring method. These coupons may then be retrieved at various time intervals and examined for corrosion damage. Although coupons can provide a qualitative indication of the condition of the structure, they do not provide direct quantitative data on the health of the structure and are costly to place and remove.

Surrogate sensing methods could measure coating barrier properties, free corrosion, and environmental properties by placing electrodes fabricated from the same metallic material as the structure near the structure of interest and collecting electrochemical and environmental measurements. Although such methods could provide an indicator of potential corrosion damage on the structure, they cannot be embedded, are only indirect measures of conditions, and are impossible to implement in applications where the structure is inaccessible.

There is a need for an in situ (e.g., on site, in place, local, etc.) apparatus, system, and method of detecting electrochemical corrosion and material or coating degradation that does not require electrical connection to the structure and can directly detect the earliest stages of coating breakdown and corrosion before damage progresses to more serious cases, e.g., pitting and cracking. It would be desirable to also distinguish between coating degradation of layers in a multilayer coating stack-up. Furthermore, it would be desirable for such a corrosion and coating condition measurement system to use wireless power and data transfer. Such technology would enable condition-based maintenance, reduce the number of costly destructive inspections, decrease the risk of a failure between inspection cycles, and support service life extension based on condition.

Example embodiments include a sensing apparatus for sensing corrosion condition information. A pair of contactless electrodes are placed on a coating on a surface of a structure or within or between one or more coatings on or over the surface of the structure. The term "embedded" as used herein includes being placed on a coating on a surface of a structure or within or between one or more coatings on or over the surface of the structure. The embedded electrodes are configured to function as sensors when activated to generate a current flow through the electrodes at multiple different frequencies.

Contactless control circuitry for co-location with the embedded electrodes is configured, when the electrodes and electronic circuitry are wirelessly activated, to transmit impedance data generated from the activated electrodes for detection by a receiver external to the structure. The impedance data is associated with corrosion and/or coating condition information of the structure and/or the one or more coatings.

In example applications, the sensing apparatus includes excitation circuitry for co-location with the embedded electrodes and configured to activate the pair of electrodes as sensors by applying a voltage potential at one or multiple frequencies between the pair of electrodes so as to excite and measure current flow between the electrodes and convert the current flow between the electrodes to an impedance measurement. The contactless control circuitry is configured to control excitation circuitry and to transmit digital impedance data, based on the impedance measurement, to an external, preferably wireless receiver.

An array of multiple pairs of contactless embedded electrodes may be placed on a coating on a surface of a structure or within or between one or more coatings on or over the surface of the structure. For such an array, the control circuitry may include a multiplexer configured to obtain measurements across any combination of pairs of electrodes.

In example applications, the control circuitry of the sensing apparatus includes a power source, e.g., an ultracapacitor, and radio frequency (RF) interface and communications circuitry configured to receive RF power and to charge the power source, e.g., ultracapacitor. The excitation circuitry and contactless control circuitry are configured to be powered by the charged power source. The contactless control circuitry is configured to provide digital data representing the impedance data to the RF interface and communications circuitry, and the RF interface and communications circuitry is configured to transmit the digital data to a data collection system over a radio interface.

The corrosion condition information may include, for example, a damage state parameter determined from a dry state impedance and a current impedance detected using the electrodes. The corrosion condition information may include an absolute or relative change in corrosion of the structure and/or the one or more coatings based on the impedance data associated with the pair of electrodes at multiple different frequencies.

The pair of contactless embedded electrodes is not connected to the structure through a direct electrical, optical, or other type of signal connection.

In example applications, the embedded electrodes in the pair are placed at a predetermined distance from each other so that current flow generated with the pair of electrodes is activated primarily through the structure and/or the one or more coatings.

In example embodiments, the sensing apparatus further includes one or more addition of nondestructive monitoring devices.

Other example embodiments include a sensing system for sensing corrosion condition information having a sensing device that includes a pair of contactless embedded electrodes for placement on a coating on a surface of a structure or embeddable within or between one or more coatings on or over the surface of the structure. Contactless circuitry is provided for co-location with the embedded electrodes and has communications circuitry for wireless communication. The sensing system further includes a data collection system, external and separated from the structure and any coatings on or over the structure, configured to wirelessly communicate with the sensing device and including a power source, control circuitry, and interface and communication circuitry. The pair of contactless electrodes is configured to function as sensors when activated to excite current flow between the electrodes at multiple different frequencies. The co-located contactless circuitry is configured to detect and convert the current flow to impedance data and wirelessly transmit the impedance data to the interface and communication circuitry of the data collection system. The impedance data is associated with a corrosion condition of the structure and/or the one or more coatings.

In example embodiments, the data collection system may be configured to transmit data and/or power via the interface and communication circuitry over a radio frequency (RF) interface to the sensing device.

Example applications include a data display system coupled to the data collection system that includes a graphical user interface configured to communicate from or to a user information regarding the coating and/or corrosion condition of the structure.

Other example embodiments include a method of sensing corrosion condition information. The method includes: locating or embedding a sensing device on a coating on a surface of a structure or within or between one or more coatings on or over the surface of the structure. The sensing device includes a pair of contactless electrodes. In some example applications, the sensing device also has co-located wireless communications and control circuitry. The pair of contactless electrodes is activated to excite current flow between the electrodes at one or more different frequencies. The control circuitry co-located or otherwise detects and converts the current flow to impedance data. The impedance data is associated with a corrosion condition of the structure and/or the one or more coatings.

In example embodiments, the sensing device transmits the impedance data to a data collection system, e.g., over a radio frequency (RF) interface. The data collection system is also external and separated from the structure and any coatings on or over the structure.

Other example embodiments include apparatus and methods of sensing corrosion condition information using a "walk-up" sensor device that is placed on a coating on a surface of a structure. The sensing device includes a pair of contactless electrodes and control circuitry that excite current flow between the electrodes at one or multiple frequencies. The control circuitry detects and converts the current flow to impedance data and provides the impedance data to a data collection system. The impedance data is associated with a corrosion condition of the structure and/or the one or more coatings.

DETAILED DESCRIPTION

The following description sets forth example embodiments for purposes of explanation and not limitation. But it will be appreciated by those skilled in the art that other embodiments may be employed apart from these specific details. In some instances, detailed descriptions of well known methods, interfaces, circuits, and devices are omitted so as not to obscure the description with unnecessary detail. Individual blocks are shown in some figures. Those skilled in the art will appreciate that the functions of those blocks may be implemented using individual hardware circuits, using software programs and data in conjunction with a suitably programmed digital microprocessor or general purpose computer, and/or using applications specific integrated circuitry (ASIC), and/or using one or more digital signal processors (DSPs). Software program instructions and data may be stored on a non-transitory, computer-readable storage medium, and when the instructions are executed by a computer or other suitable processor control, the computer or processor performs the functions associated with those instructions.

The term signal is used herein to encompass any signal that transfers information from one position or region to another in an electrical, electronic, electromagnetic, or magnetic form. Signals may be conducted from one position or region to another by electrical or magnetic conductors, but the broad scope of signals also includes light and other electromagnetic forms of signals and other signals transferred through non-conductive regions due to electrical, electronic, electromagnetic, or magnetic effects. The broad category of signals includes both analog and digital signals: An analog electrical signal includes information in the form of a continuously variable physical quantity, such as voltage; a digital electrical signal includes information in the form of discrete values of a physical characteristic, which could also be, for example, voltage.

Unless the context indicates otherwise, the terms circuitry and circuit are used herein to refer to structures in which one or more electronic components have sufficient electrical connections to operate together or in a related manner. In some instances, an item of circuitry can include more than one circuit. An item of circuitry that includes a processor may sometimes be analyzed into hardware and software components; in this context, software refers to stored or transmitted data that controls operation of the processor or that is accessed by the processor while operating, and hardware refers to components that store, transmit, and operate on the data. Circuitry can be described based on its operation or other characteristics. For example, circuitry that performs control operations is sometimes referred to as control circuitry, and circuitry that performs processing operations is sometimes referred to as processing circuitry.

In general, sensors, processors, and other such items may be included in a system in which they are operated automatically or partially automatically. The term system refers to a combination of two or more parts or components that can perform an operation together. A system may be characterized by its operation.

As described in the background and summary section, known methods for detecting the early stages of electrochemical corrosion often use electrochemical polarization techniques that require a direct electrical connection to the metallic structure under test. The contactless technology described here uses embedded electrodes and associated control circuitry that do not require a wired or cable signal connection to detect corrosion. Although it is known that an electrode can be polarized by placing it within an electric field generated by applying a potential to two external electrodes, it is typically recognized as stray current corrosion. For example, this form of corrosion can be observed when a pipeline is buried near a structure that is protected with an impressed current system. Stray currents from this system can travel into the nearby pipeline initiating corrosion. Accordingly, stray current corrosion is conventionally seen as a problem. The inventors, however, developed a technique that uses these basic electromagnetic field theory principles to instead sense corrosion. The technique also preferably uses wireless power and communications technology to create a contactless embedded sensing system that eliminates any through penetrations on the structure, coverings, insulation, or protection system. This also enables monitoring of moving or rotating components for corrosion coating performance not possible using conventional monitoring approaches. Advantageously, the technology detects the early stages of corrosion without a direct electrical connection to the substrate.

A non-limiting example monitoring system includes contactless or non-contact corrosion sensing electrodes for in-place, local assessment of structural corrosion and/or structural coating corrosion without a direct electrical, optical, or other type of signal connection to the structure. The term "direct signal connection" means a hardwire connection such as a wire, cable, fiber, etc. The terms "contactless" and "non-contact" mean that the electrodes (and in some example embodiments associated control circuitry) are not hardwire-connected to any wire, cable, fiber, etc. extending to the surface a direct signal connection as defined above.

The electrodes can be fabricated from a relatively inert alloy or noble material such as gold so as to be corrosion resistant. The electrodes can be used alone as one pair or as part of an array for distributed sensing over a large structure to assess extent and location of coating degradation and structure corrosion. The contactless corrosion sensing system can also be used to characterize materials in accelerated or service performance testing and can be used on moving or rotating components. All communications with and power (if external power is required) to the electrodes (and in some example embodiments associated control circuitry) is accomplished wirelessly. Wireless means that communication signals and power (if external power is required) are transferred without a wire, cable, fiber, etc.

The embedded electrodes (and co-located control circuitry, in example embodiments that use co-located control circuitry) can be powered, in one non-limiting embodiment, using mutual inductance near field coupling with an external monitoring system. When the embedded electrodes are in proximity with an external monitoring system, the monitoring system triggers measurements to be collected. Far field electromagnetic radio frequency methods may also be used to power the system.

A non-limiting example embodiment co-locates control circuitry with the embedded electrodes to form a sensing system. In one example embodiment, the embedded electrodes and co-located control circuitry are embedded as a module on or within the structure. In another example embodiment, the embedded electrodes and co-located control circuitry are a part of a walkup measurement unit that can be placed on the surface of the structure and/or structure coating to make corrosion measurements.

The control circuitry in one example includes Passive Low Frequency Interface circuitry (PaLFI), a power source, a microcontroller, and excitation circuitry. In example implementations, the sensing system is preferably designed with a conformal, low-profile form factor to be permanently encased and have minimal impact on the material surrounding the structure. Wireless power (if external power is required) and wireless data signal transfer through the material surrounding the electrodes coupled with the contactless sensing eliminates the need for electrical conductors, optical fibers, etc. to penetrate the surrounding material or connect with the structure and thereby introduce additional possible failure points.

Wireless power (if external power is required) and wireless signal transfer system in example embodiments may be interrogated using a handheld wireless reader external to the surface and coverings of the structure. (The handheld wireless reader is a different embodiment that the walkup measurement sensing device). The example handheld wireless reader embodiment includes a reader with a transceiver device that wirelessly powers the embedded instrumentation using near field electromagnetic induction to execute measurements and transfer data. Alternative example embodiments use far field readers, batteries, or other energy sources to power the embedded sensor system. A user-friendly graphical user interface (GUI) presents and preferably also interprets the acquired sensor data in a format in which users can take appropriate action. The GUI also preferably provides a time history of the condition of the structure. Example embodiments may also include a separate indication of damage using additional nondestructive sensing techniques, e.g., those that use ultrasonics or eddy currents.

Figure 1:
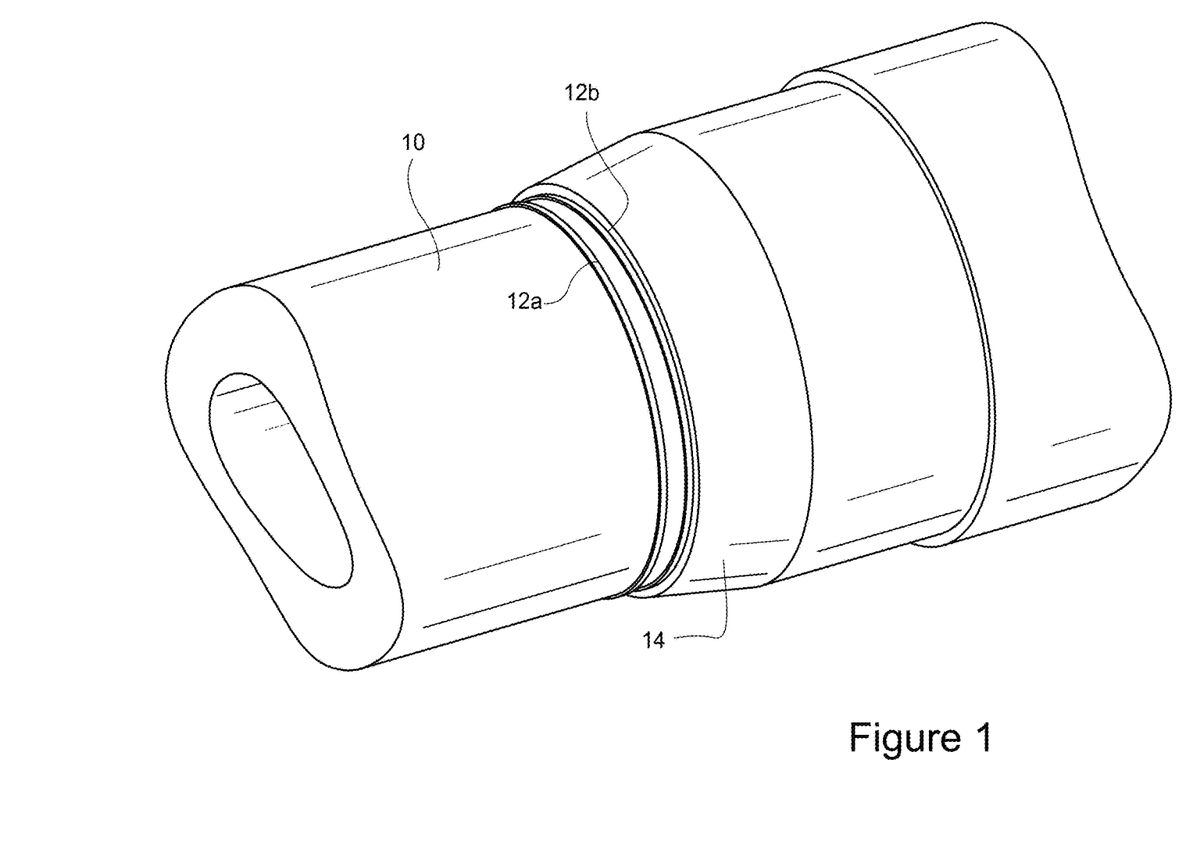
FIG. 1 shows an example ring electrode configuration on a propulsion shaft.
Figure 2:
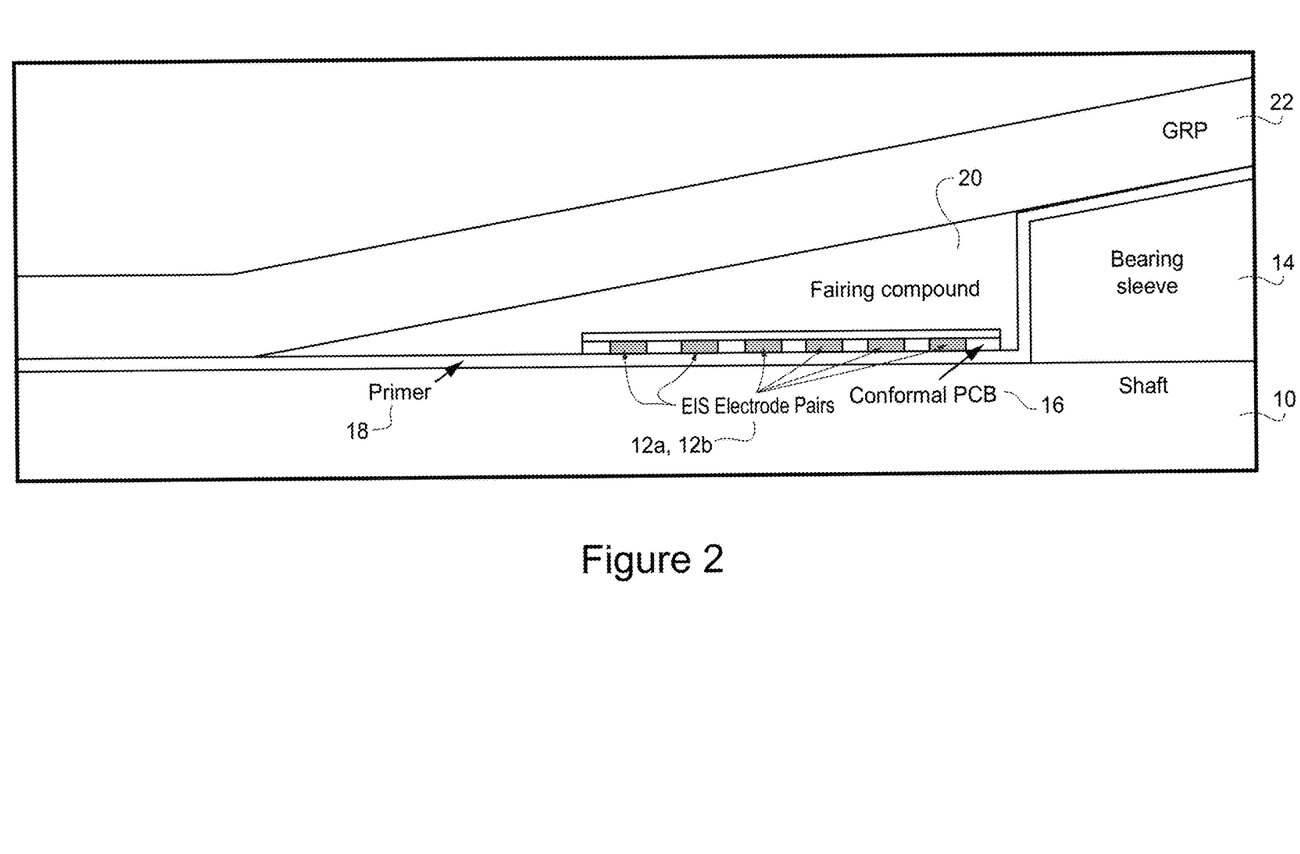
FIG. 2 shows an example contactless, embedded electrode measurement system where electrode pairs are embedded in a fairing compound for monitoring water ingress and steel corrosion of a propulsion shaft.

In an example embodiment of a sensing system for measuring and monitoring the condition of a ship propulsion shaft 10, (which is a non-limiting example 10 of a monitored structure), two pairs of electrodes 12a and 12b encircling the shaft, as shown in FIG. 1, are embedded at the interface between two layers of coatings, as shown in FIG. 2. FIG. 1 shows an example ring electrode configuration adjacent to a bearing sleeve 14 on the propulsion shaft 10. The shaft 10 may be made for example of steel, and the bearing sleeve 14 may be made for example of a combination of copper and nickel (Cu/Ni).

FIG. 2 shows an example measurement system for monitoring water ingress and steel corrosion embedded in an example multilayer coating stack-up for the propulsion shaft 10. The example includes primer and elastomeric coatings 18 that may be made from a low-viscosity primer for polysulfides and an epoxy cured with polysulfides, respectively, a fairing compound layer 20 made from a polysulfide sealing compound, and a glass-reinforced plastic (GRP) layer 22 made from an epoxy laminating resin. In this example, three pairs of Electrochemical Impedance Spectroscopy (EIS) electrodes are shown on a conformal printed circuit board (PCB) 16. In this example embodiment, electrodes have 0.2 mm spacing, with the electrode pairs spaced 22 mm apart.

Figure 3A:
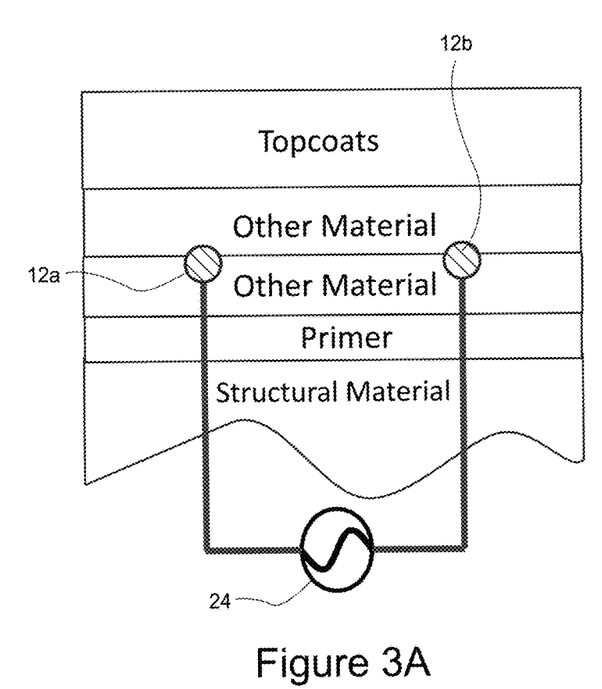
FIG. 3A shows an example cross section with an embedded electrode pair.
Figure 3B:
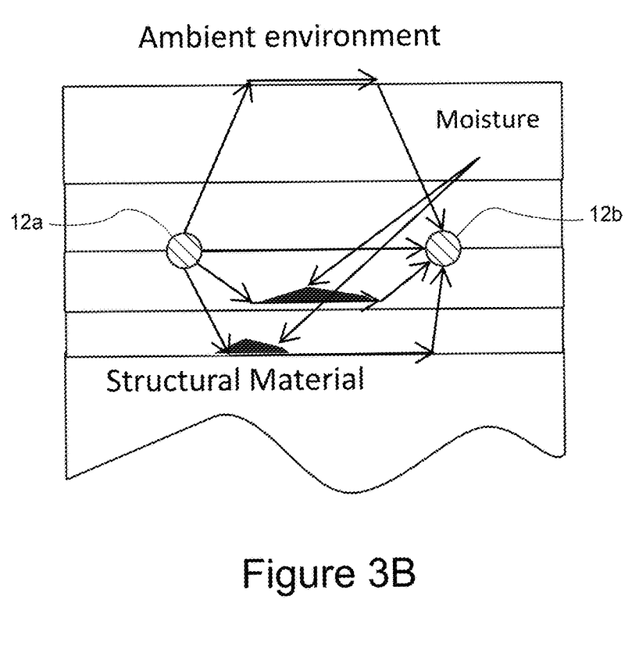
FIG. 3B shows example current pathways between the electrodes.

FIG. 4A shows an example cross section with an embedded electrode pair 12a and 12b (shown as cross-hatched circles) connected to a current source. FIG. 3B shows current pathways (with arrows) between the two electrodes 12a and 12b. The electrodes 12a and 12b do not contact the structure but instead are embedded in coating(s) covering at least some portion above the structure surface.

FIG. 3A shows how an impedance is measured between the two embedded electrodes 12a and 12b by using electronics embedded with the electrodes within the coatings(s)

covering 24 to apply a low voltage AC signal and sweep the frequency from 0.1 Hz to $10^5$ Hz. The overall impedance measured is a function of the condition of the structure (labeled structural material in FIGS. 3A and 3B) and surrounding material and may depend on electrochemical, ionic, and/or electrical properties. Multiple interfaces and current pathways exist that have unique impedance properties that may change with time and condition of the coatings and structure.

In example embodiments, the pair of electrodes 12a and 12b is preferably optimized to increase sensitivity to the current pathway through the structural material and to minimize current pathways through the surrounding material such as the primer, other materials, and topcoats labeled in FIG. 3A and pathways shown in 3B. This is accomplished by adjusting the spacing between the individual electrodes in a pair, adjusting the spacing between the pairs of electrodes, and/or by modifying the proximity of the electrodes to the substrate to obtain an optimal spacing and distance for direct measurement of structural alloy corrosion. By making the spacing closer together and distance from the surface shorter, an optimal distance can be obtained such that current pathways across the coating interface have a high impedance and are less likely than current pathways passing through the structural material that have a lower impedance.

Example embodiments may further include one or more nondestructive sensing techniques, such as ultrasonics or eddy currents, utilized in parallel with the contactless embedded electrodes for further characterizing material degradation and corrosion.

An example embodiment of contactless corrosion measurement is now described with reference to the function block diagram shown in FIG. 4. The example system includes an optional data consolidation and display system 30, a data collection system (DCS) 32 (also referred to as a reader or transceiver), and an embedded sensor system (ESS) 34 including control and communication electronics and sensing elements.

The embedded sensor system 34 includes embedded sensors such as one or more pairs of electrodes like those in the example in FIGS. 2 and 3 along with Passive Low Frequency Interface (PaLFI) circuitry 36 (an example PaLFI is available from Texas Instruments) that provides near-field wireless power transfer and communications with embedded control circuitry and sensors 44, e.g., electrodes. The embedded sensor system 34 includes an ultracapacitor 38 coupled to receive and store energy from the PaLFI circuitry 36, a microcontroller 40 powered via the ultracapacitor 38 and coupled to communicate digital data with the PaLFI circuitry 36, sensor excitation circuitry 42 coupled to the ultracapacitor, and the embedded sensors 44 powered via the excitation circuitry 42.

In other example embodiments, the ultracapacitor may be replaced by a battery or a very long term independent power source.

Figure 4:
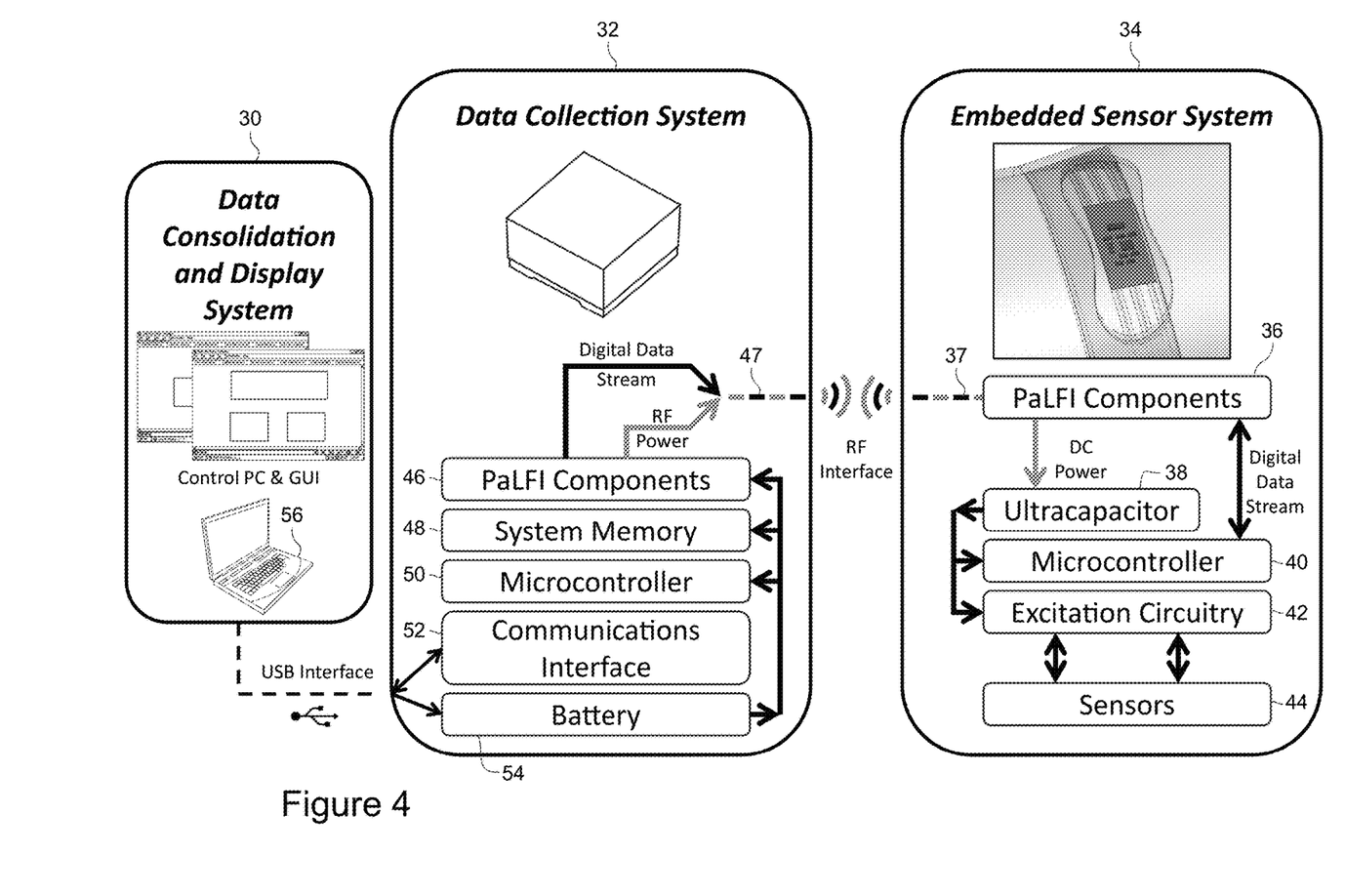
FIG. 4 shows another example embodiment of a contactless corrosion measurement system that includes an embedded sensor system (ESS), a data collection system (DCS), and a data consolidation and display system (DCDS).

The data collection system 32 in the example of FIG. 4 acts as a battery-powered wireless communication base station, wirelessly providing power to the embedded sensor system 34. Antennas 47, 37 in both the data collection system and embedded sensor system, respectively, use mutual inductive coupling at a nominal frequency, e.g., 134.2 kHz, that allows for collection of radio frequency (RF) energy at the embedded sensor system 34. Other frequencies may be used. This in turn charges the ultracapacitor 38 within the embedded sensor system 34 for short-term energy storage. Once sufficient energy is stored in the ultracapacitor 38, the electronic circuitry within the ESS 34, including the microcontroller 40, is activated, triggering pre-defined signal waveforms generated by the excitation circuitry 42 at varying frequencies that are applied across the sensors 44, in this example EIS electrodes. The resultant current response is measured by elements of the excitation circuitry and converted to an impedance measured across the embedded corrosion sensors (and one or more non-destructive sensing systems, if used).

Although one pair of electrodes may be used, an array of pairs of electrodes may be also be used. To allow several combinations of electrode measurements, a low-voltage multiplexer may be included in the excitation circuitry to sequentially obtain measurements across pairs of electrodes in the array, e.g., with different electrode spacings.

Electrochemical impedance spectroscopy (EIS) collects kinetic information on physiochemical processes occurring in an electrochemical system, such as electron and ion transport and heterogeneous reactions. EIS is performed by applying a small AC potential to the electrochemical system and measuring the impedance over a range of frequencies. In a non-limiting example the frequency range is 0.1 Hz to $10^5$ Hz. Impedance can be thought of as the resistance to flow of the AC signal. The measured impedance can be processed using an electrical circuit composed of resistors (R), capacitors (C), and inductors (L) to determine additional quantitative data on physiochemical processes occurring. In particular for corrosion processes, changes in the shape of the impedance curve, such as a plateau forming at low frequencies and a sharp drop in the impedance measured at low frequencies can be indicative of corrosion occurring.

The sensor measurements (and non-destructive measurements if used) are digitized by the microcontroller 40, and transmitted wirelessly back via the PaLFI circuitry 36 and a radio frequency (RF) interface to the DCS 32. Upon completion of sensor measurements and data transmission, the ultracapacitor 38 self-discharges, and the microcontroller 40 enters a shutdown mode until charging is re-initiated by the DCS 32.

In a non-limiting example embodiment, the DCS 32 is handheld. During system operation and measurement initiation, the DCS 32 is placed in proximity to the structure under test and aligned with the ESS antenna 37. This limits the distance between the two system antennas, 37, 47, providing for the satisfactory energy coupling between the two antennas. The output energy of the DCS 32 base station can induce a relatively high current (e.g., 116 mA) in the ESS antenna coil 37. It is also possible to permanently mount the DCS 32 near the ESS 34 to obtain automated data collection on stationary or moving structures.

Assuming an example ESS 34 using a capacitor value of 0.06 F with a 0.5 ohms equivalent series resistance, it takes approximately 174 seconds to charge the ultracapacitor 38 from an initial value of 0.1 Vdc up to 3.0 Vdc, given a charge current of 1 mA. For an assumed example ESS circuitry load of approximately 600 ohms, or 5 mA initial current consumption from the storage capacitor, and a capacitive voltage discharge from 3.0 Vdc to 1.85 Vdc, the capacitive storage element can provide sufficient electrical power to operate the circuitry for 17.4 seconds. For the measurements in this example, this is sufficient time to initiate system operations, excite sensor elements and take measurements, process and format the measurements into data messages, and wirelessly report the measurement results back to the DCS.

Firmware (not shown) within the example ESS 34 provides an interface between the microcontroller 40 and the PaLFI device 36 through a standard serial peripheral interface (SPI) port that is part of the PaLFI circuitry. An SPI is an interface bus commonly used to send data between microcontrollers.

Figure 5:
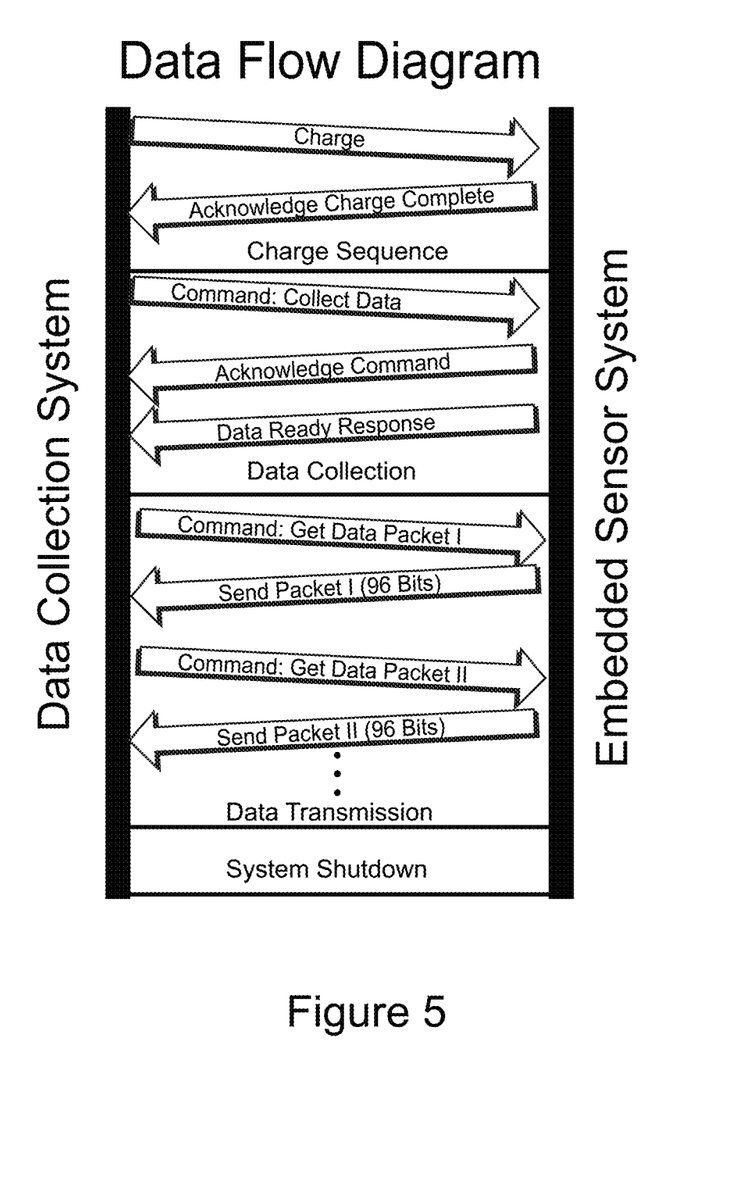
FIG. 5 is a data flow diagram showing example signal messages between a data collection system (DCS) and an embedded sensor system (ESS).

FIG. 5 shows a data flow diagram of example signaling between the data collection system 32 and the embedded sensor system 34. Once charging of the embedded sensor system 34 by the data collection system 32 has occurred and is acknowledged, the PaLFI 36 receives and acknowledges a "Collect Data" command from the data collection system 32 over the RF interface. In response, the ultracapacitor 38 provides voltage to the excitation circuitry 42. The microcontroller 40 controls the excitation circuitry 42 to generate appropriate AC excitation signals for the embedded electrodes sensors 44. Measurements of impedance collected over a frequency range of 0.1 Hz to $10^5$ Hz from the sensors 44 are digitized and recorded using the microcontroller onboard ND converters. Following this sensor data collection at the ESS 34, the PaLFI circuitry 36 wirelessly transfers sensed impedance data back to the DCS 32, e.g., in one or more data packets, until the sensor data transfer is completed. A non-limiting example packet may have 96 bits.

The sensor impedance data is recorded in non-volatile system memory 48 on the DCS 32, and is ready for retrieval via the system communications (e.g., USB) interface 52. At the completion of a successful data transmittal, the ESS 34 shuts down, and the embedded ultracapacitor 38 self-discharges until the DCS 32 re-charges it and requests another measurement.

The physical construction of the ESS circuitry excluding the electrodes is implemented in a non-limiting example embodiment using flexible, conformal circuitry. For example, the ESS circuitry uses a double-sided flex circuit with electronic components installed on one of the two conductor layers. Both top and bottom layers of the circuitry are protected by cover-layers and conformal coating to maintain electrical isolation from surrounding materials and to guard the electronic components and circuitry wiring from any corrosive ingress.

Since the corrosion processes being monitored by the contactless embedded electrodes 44 are typically slow, the example embodiment of the measurement and monitoring system collects periodic sensor measurements of impedance.

For continuous measurements of impedance, and thus, the corrosive condition of the monitored structure, alternate example embodiments of the corrosion monitoring and measurement system can use a permanently-mounted DCS 32 transceiver (rather than handheld), embedded batteries, or other energy sources such as solar cells or vibration energy scavenging to power the electrodes.

The ESS circuitry may also include a memory with sufficient storage to store the data for a periodic download. Data may be wirelessly transmitted to a data collection system for processing and storage.

The data consolidation and display system or the graphical user interface (GUI) 30 is used for processing and viewing the data from the contactless embedded electrodes. Once the DCS 32 is ready for data retrieval, it is connected to a laptop via the system communications (e.g., USB) interface 52. On the laptop, plots can be viewed that display the impedance at certain frequencies and over various frequency ranges, area values (integration of the impedance response), and/or other parameters extracted.

By monitoring how features of the sensed impedance response of the structure have changed with time, insight into the condition of the structure may be determined in terms of corrosion and material degradation. For example, an initial decrease in measured impedance values is expected with water ingress into the coating. However, with time further decreases in impedance and changes in the shape of the impedance curve, such as a plateau developing at low frequencies may be indicative of further detrimental water ingress and corrosion. In alternative example embodiments, one or more other nondestructive techniques could be used in combination with contactless embedded electrodes to further characterize coating condition, corrosion, and damage to the structure.

The contactless embedded monitoring system examples described above provide measurements of impedance over one frequency or a range of multiple frequencies linked to the condition of the overall structure including the early stages of coating breakdown and corrosion degradation. The example monitoring system is particularly useful for applications where the coated metallic structure is difficult to access or moving and/or where a direct electrical connection is impractical and/or would degrade the overall performance of the structure, such as a substrate with a multilayer coating stack-up, insulating cover, a coated alloy embedded in concrete or soil, or a rotating shaft. As described above, the embedded electrodes may be used as a single pair or as an array for distributed sensing over a large structure or to detect degradation throughout multiple layers.

The contactless embedded electrodes may be used alone in a corrosion monitoring and measurement system as an early indicator of electrochemical condition or together with another nondestructive technique that detects later stages of corrosion such as pitting and cracking to further validate sensor output.

Although the example embodiment in FIG. 4 shows the embedded sensor system 34 where control circuitry (e.g., 36, 38, 40, and/or 42) is co-located with the embedded electrode sensors 44, other example embodiments include the embedded electrode sensors 44 with the control circuitry not co-located with the embedded electrode sensors 44. Instead, the control circuitry may be a part of the data collection system 32 with the embedded electrode sensors 44 being activated when the data collection system 32 is brought in proximity with the embedded electrode sensors 44.

Other example embodiments include apparatus and methods of sensing corrosion condition information using a "walk-up" sensor device that is placed on a coating on a surface of a structure. The sensing device includes a pair of contactless electrodes and control circuitry that excite current flow between the electrodes at one or multiple frequencies. The control circuitry detects and converts the current flow to impedance data and provides the impedance data to a data collection system. The impedance data is associated with a corrosion condition of the structure and/or the one or more coatings.

An additional example application of the monitoring system is accelerated corrosion testing for characterizing the performance of coatings for the development and acceptance of new materials. Presently, there is a lack of quantitative data during accelerated testing to accurately understand the corrosion processes and material interactions that are occurring. In particular, for multilayer coating stack-ups it is difficult to track the corrosion of the substrate and the moisture and ionic diffusion through the stack-up. Chemical, mechanical, and thermal degradation processes may affect each layer and interface differently, and the dominant failure mode may be associated with an individual layer or specific material interactions. The contactless embedded electrodes may be embedded throughout the stack-up thickness within layers and/or at interfaces between layers to obtain impedance measurements that would reflect the evolution of corrosion and coating properties with time and exposure conditions.

A non-limiting example embodiment monitoring or measurement system may be tailored to an application for ship propulsion shafts that are steel shafts coated with multilayer protection systems. These rotating shafts are susceptible to pitting and fatigue damage. This damage is caused by the intrusion of seawater into the coating that, when it reaches the surface of the shaft, can initiate galvanic corrosion between the steel shaft and a Cu/Ni bearing sleeve. Fleet-wide maintenance often requires drydocking ships at ten year intervals for full shaft removal and inspection to determine whether the GRP covers that protect the shaft-sleeve interface have successfully prevented seawater intrusion and subsequent shaft pitting/fatigue damage. Often, the inspection reveals no water ingress or shaft damage, meaning that the sleeve was removed before the end of its useful operating life. Conversely, some inspections have revealed significant damage, evidencing cover failure well before the end of expected design life. The instant technology provides an in situ nondestructive method to monitor shaft health more frequently.

The embedded electrodes can be used to detect, e.g., coating degradation, seawater ingress, and corrosion of a propulsion shaft by applying a low voltage alternating current (AC) signal between the two electrodes embedded in the coating on the structure.

Figure 6:
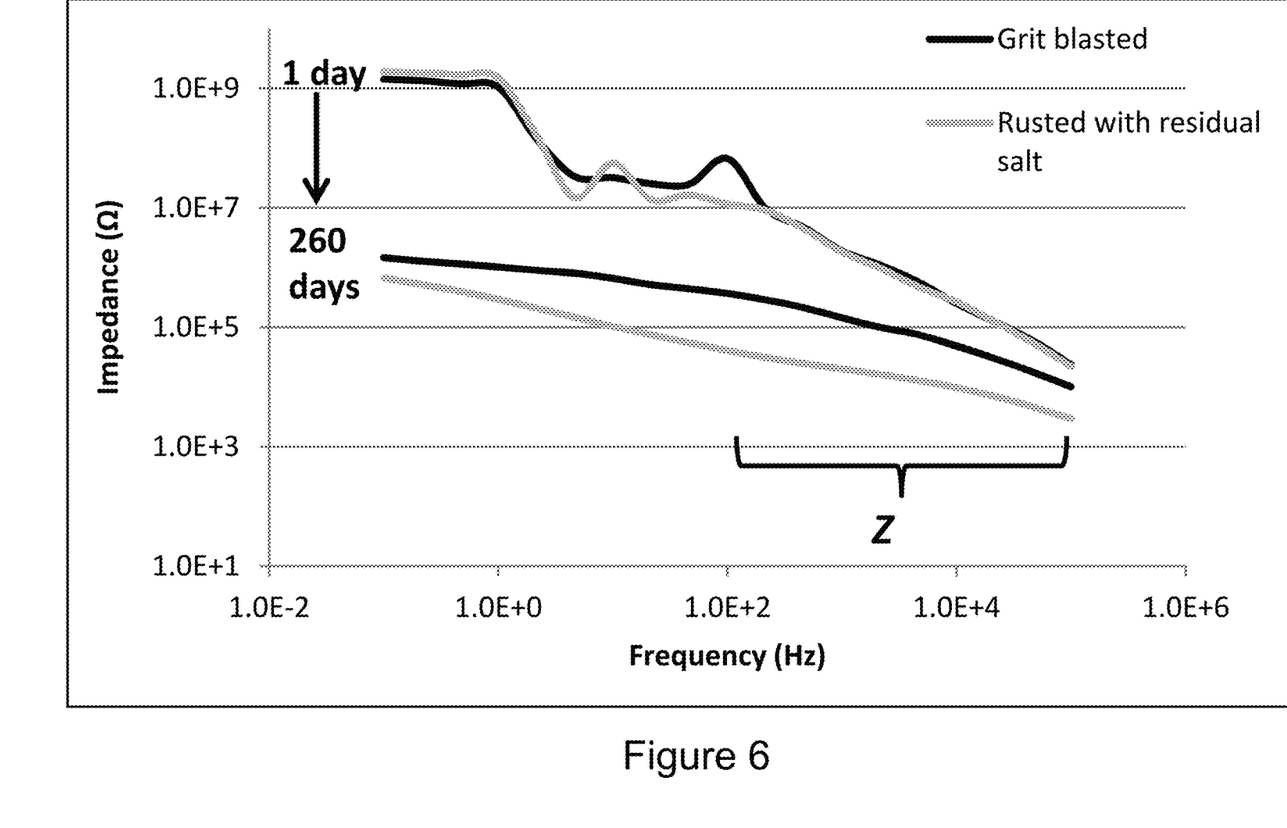
FIG. 6 is a graph showing an example electrochemical impedance spectroscopy scan using noncontact embedded sensing electrodes on steel shafts with different initial surface conditions (grit blast and rusted with residual salt) and a base primer and different elastomeric coatings submerged in a sodium chloride salt solution.

In example embodiments, excitation of the noncontact embedded sensing electrodes preferably includes multiple different frequencies to obtain barrier properties and corrosion behavior. The coating condition and corrosion may be quantified by examining the change over time in impedance values measured at different frequencies and frequency ranges or area values obtained by integrating the impedance response. In further example embodiments, coating condition and corrosion are quantified by performing curve fits and extracting parameters based on deterministic or empirically derived models. FIG. 6 is a graph showing an example electrochemical impedance spectroscopy scan and the impedance values obtained using noncontact embedded sensing electrodes on a steel shaft with base primer and elastomeric coating submerged in sodium chloride. Two example shafts for monitoring were prepared with a relatively better coating system (e.g., grit blast) and a relatively worse coating system (e.g., rusted with residual salt).

Features of the impedance response with frequency may be used to obtain absolute measures of the condition or relative changes in the coating and corrosion at the location where the electrodes are positioned. In an example embodiment, the coating and/or corrosion condition is assessed using a non-dimensional damage state parameter ($\delta$) calculated in accordance with the formula below from a dry state impedance ($Z_{dry}$) relative to a current impedance ($Z_n$) evaluated at each time interval.

$$\delta = \frac{\text{Log}(Z_{dry}) - \text{Log}(Z_n)}{\text{Log}(Z_{dry})}$$

Figure 7:
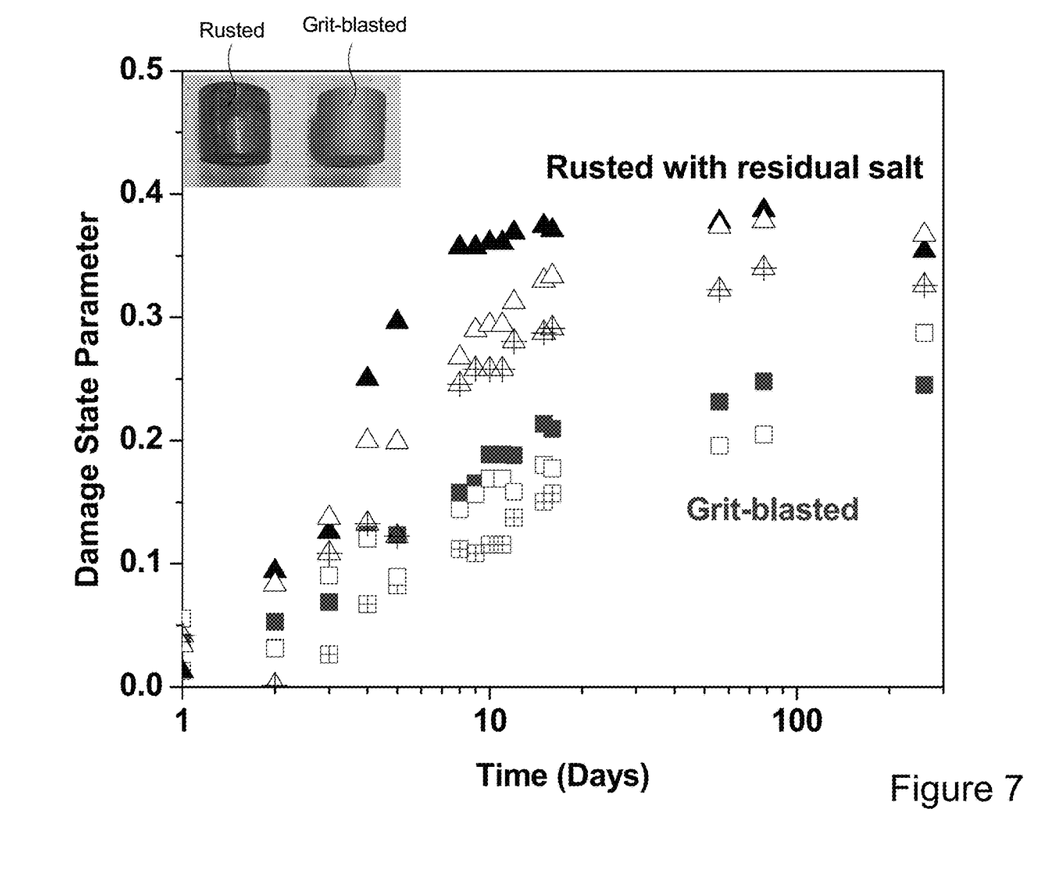
FIG. 7 is a graph showing example damage state parameters calculated for rusted and grit blasted shaft samples indicating an example of the ability of contactless, embedded sensing electrodes to differentiate between conditions of the coating and steel shaft.

FIG. 7 shows example damage state values calculated for rusted and grit blasted shaft samples tested in FIG. 6. These shaft samples with different initial starting conditions, either rusted or grit blasted surfaces, then had the electrodes and additional protective coatings applied before initiation of the test in sodium chloride. The rusted shaft samples should have poor coating adhesion and thus worse coating properties. Water ingress and corrosion should therefore proceed more quickly on these samples than on the grit blasted shafts. In FIG. 6, this is observed with the rusted shaft measuring lower impedance values across all frequencies than the grit blasted shaft. Both the x and y axis in FIG. 6 are on a logarithmic scale. Damage state values calculated for these two types of shafts, (grit blasted indicated with square symbols and rusted indicated with triangles), indicate that the example embedded sensing electrodes detect and differentiate between conditions of the coating and steel shaft. After a period of initiation of approximately ten days, where both grit blasted and rusted shafts have similar damage state parameters, a difference in damage state parameter is observed with the rusted shafts having higher damage state values.

Figure 8:
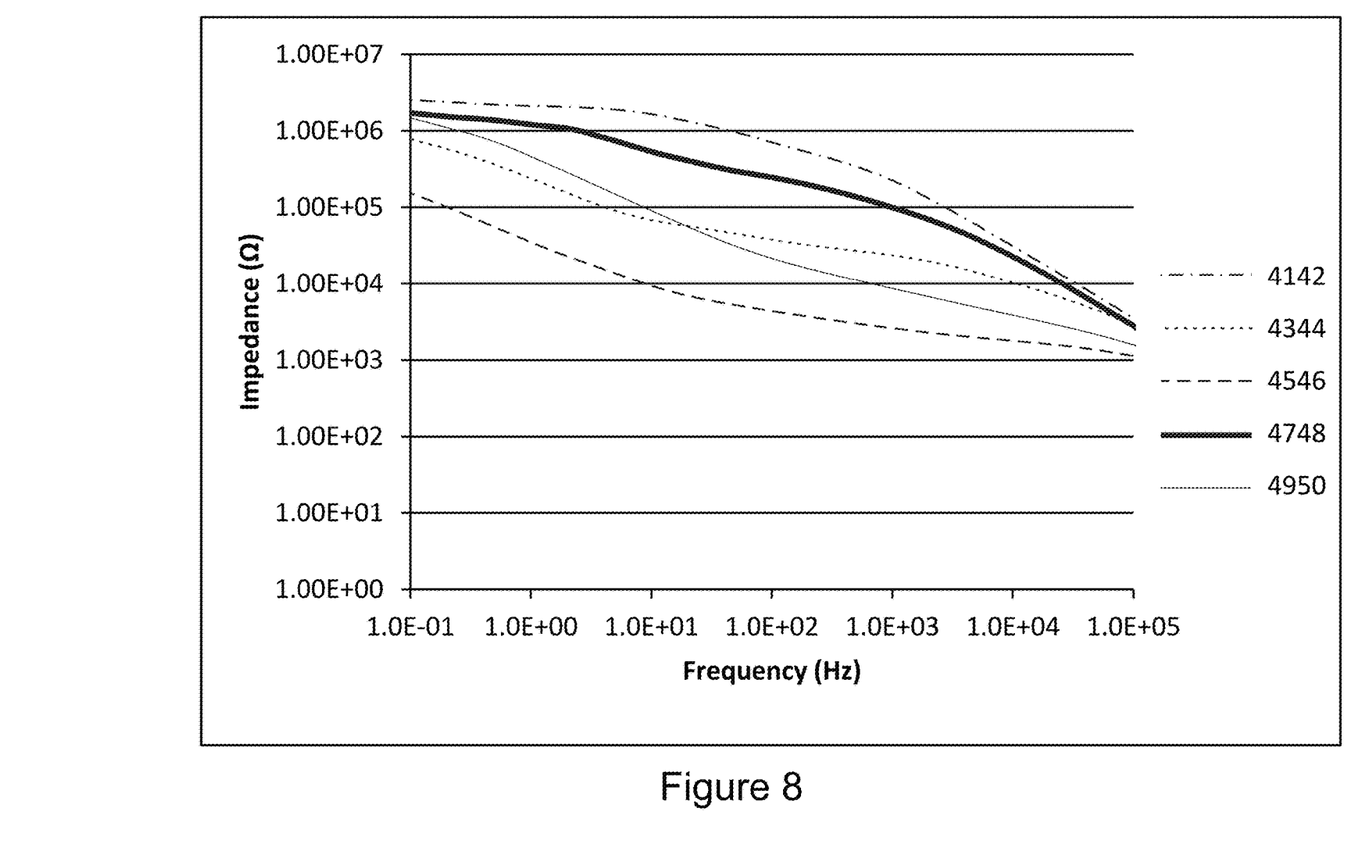
FIG. 8 is a graph showing an example electrochemical impedance spectroscopy scan using noncontact embedded sensing electrodes on a steel shaft with base primer and elastomeric coating submerged in a salt solution.
Figure 9:
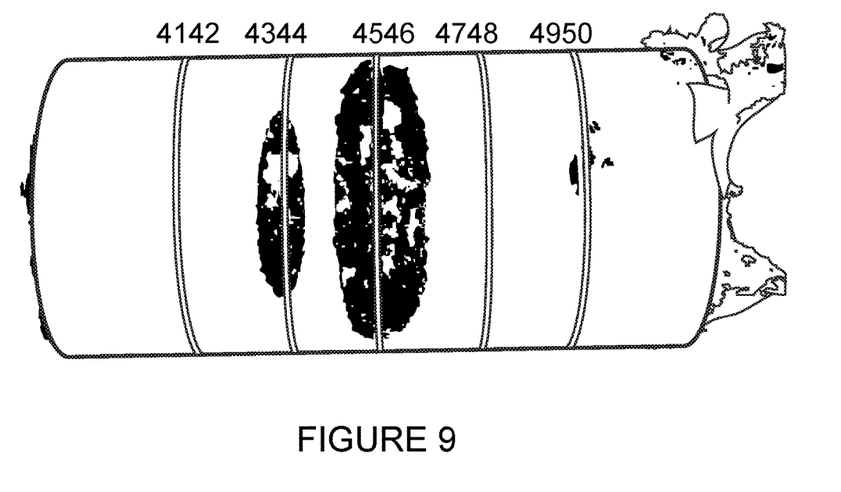
FIG. 9 shows the shaft in FIG. 8 prepared with pre-corroded regions of three different sizes located underneath the sensing ring electrode pairs.

FIG. 8 and FIG. 9 further demonstrate that measured low frequency impedance values can be utilized to differentiate between corroded regions of different areas. FIG. 8 is a graph showing an example electrochemical impedance spectroscopy scan using noncontact embedded sensing electrodes on a steel shaft with base primer and elastomeric coating submerged in a salt solution.

FIG. 9 shows the shaft in FIG. 8 prepared with pre-corroded regions of three different sizes located underneath the sensing ring electrode pairs. The shaft had pre-corroded regions of three different areas underneath three pairs of ring electrodes. The impedance measured at low frequencies for this shaft correlated well with defect area and location. The impedance measured between the electrodes above the largest defect was the lowest. The electrodes above the medium defect measured a slightly higher impedance value, and the impedance between the electrodes above the smallest defect aligned with the other electrode pairs that did not have defects under them.

Although various embodiments have been shown and described in detail, the claims are not limited to any particular embodiment or example. None of the above description should be read as implying that any particular member, step, range, or function is essential such that it must be included in the claims scope. The scope of patented subject matter is defined only by the claims. The extent of legal protection is defined by the words recited in the allowed claims and their equivalents. All structural and functional equivalents to the members of the above-described preferred embodiment that are known to those of ordinary skill in the art are expressly incorporated herein by reference and are intended to be encompassed by the present claims. Moreover, it is not necessary for a device or method to address each and every problem sought to be solved by the technology described, for it to be encompassed by the present claims. No claim is intended to invoke paragraph 6 of 35 USC §112 unless the words "means for" or "step for" are used. Furthermore, no embodiment, feature, component, or step in this specification is intended to be dedicated to the public regardless of whether the embodiment, feature, component, or step is recited in the claims.

References incorporated herein by reference:

[1] G. D. Davis and C. M. Dacres, "Electrochemical sensors for evaluating corrosion and adhesion on painted metal structures," U.S. Pat. No. 5,859,537 January-1999.

[2] Y. Y. Steven, M. R. Matthews, and G. A. Shreve, "Coating impedance monitoring system," U.S. Pat. No. 7,477,060 January-2009.

[3] G. D. Davis, R. C. Dunn, and R. A. Robert, "COATING MONITOR FOR EVALUATING THE EFFECTIVE- NESS OF PROTECTIVE COATINGS," U.S. patent application Ser. No. 13/376,424 June-2010.
[4] D. Wang, Y. Y. Steven, and G. A. Shreve, "Method and system for electrochemical impedance spectroscopy," U.S. Pat. No. 7,877,009 January-2011.
[5] T. A. Wavering, F. J. Friedersdorf, C. L. Bopp III, and others, "Wireless corrosion sensor," U.S. Pat. No. 8,085,165 December-2011.
[6] K. Allahar, Q. Su, and G. Bierwagen, "Non-substrate EIS monitoring of organic coatings with embedded electrodes," *Progress in Organic Coatings*, 67, 2, pp. 180-187, 2010.
[7] C. Andrade, I. Martinez, and M. Castellote, "Feasibility of determining corrosion rates by means of stray current-induced polarisation," *Journal of Applied Electrochemistry*, 38, 10, pp. 1467-1476, 2008.
[8] A. Nogueira, X. R. Nóvoa, and C. Pérez, "On the possibility of using embedded electrodes for the measurement of dielectric properties in organic coatings," *Prog. Org. Coat.*, 59, 3, pp. 186-191, 2007.
[9] C. S. Brossia, D S. Dunn, "Apparatus and Method for Detecting the Degradation of a Coating Using Embedded Sensors," U.S. Pat. No. 6,911,828 June-2005.
[10] N. F. Materer, A. W. Apblett, "Passive wireless corrosion sensor," U.S. Pat. No. 7,675,295 March-2010.

The invention claimed is:

1. A sensing apparatus for sensing corrosion condition information, comprising:
a pair of contactless electrodes for placement on a coating on a surface of a structure or within or between one or more coatings on or over the surface of the structure and configured to function as sensors, which when activated, conduct a current flow at one or more frequencies,
wherein impedance related data generated from the activated electrodes is associated with corrosion condition information of the structure and/or the one or more coatings.

2. The sensing apparatus in claim 1, further comprising: contactless control circuitry for co-location with the electrodes and configured, when the electrodes are activated, to transmit impedance related data generated from the activated electrodes for detection by a receiver external to the structure.

3. The sensing apparatus in claim 2, wherein the contactless control circuitry wirelessly transmits the impedance related data to a wireless receiver over a radio interface.

4. The sensing apparatus in claim 2, further comprising:
an array of multiple pairs of contactless electrodes for placement on a coating on a surface of a structure or within or between one or more coatings on or over the surface of the structure,
a multiplexer in the contactless control circuitry configured to obtain measurements across the pairs of electrodes.

5. The sensing apparatus in claim 2, further comprising:
excitation circuitry configured to activate the pair of electrodes by applying a low voltage potential at one or multiple different frequencies between the pair of electrodes so as to excite and measure current flow between the electrodes and convert the current flow between the electrodes to an impedance measurement, and
wherein the contactless control circuitry is configured to control the excitation circuitry and to transmit digital impedance data, based on the impedance measurement, to the external receiver.

6. The sensing apparatus in claim 5, further comprising:
a power source,
radio frequency (RF) interface and communications circuitry configured to receive RF power and to charge the power source, and
wherein the excitation circuitry and contactless control circuitry are configured to be powered by the charged power source.

7. The sensing apparatus in claim 6, wherein the contactless control circuitry is configured to provide digital data representing the impedance data to the RF interface and communications circuitry, and
wherein the RF interface and communications circuitry is configured to transmit the digital data to a data collection system over a radio interface.

8. The sensing apparatus in claim 1, further comprising:
control circuitry configured, when the electrodes are activated, to detect impedance related data generated from the activated electrodes.

9. The sensing apparatus in claim 1, wherein the corrosion condition information includes a damage state parameter determined from a dry state impedance and a current impedance detected using the electrodes.

10. The sensing apparatus in claim 1, wherein the corrosion condition information includes an absolute or relative change in corrosion of the structure and/or the one or more coatings based on the impedance related data associated with the pair of electrodes at multiple different frequencies.

11. The sensing apparatus in claim 1, wherein the pair of contactless electrodes is not connected to the structure through a direct electrical, optical, or other type of signal connection.

12. The sensing apparatus in claim 1, wherein the electrodes in the pair are placed at a predetermined distance from each other so that current flow generated with the pair of electrodes are activated is primarily through the structure and/or the one or more coatings.

13. The sensing apparatus in claim 1, further comprising one or more addition nondestructive monitoring devices.

14. The sensing apparatus in claim 1, wherein the pair of electrodes are embedded between two coatings on or over the surface of the structure.

15. A sensing system for sensing corrosion condition information, comprising:
a sensing device including:
a pair of contactless electrodes for placement on a coating on a surface of a structure or embeddable within or between one or more coatings on or over the surface of the structure, and
contactless circuitry for co-location with the electrodes and having communications circuitry for wireless communication, and
a data collection system configured to communicate with the sensing device,
wherein the pair of contactless electrodes is configured to function as sensors when activated by the data collection system to excite current flow between the electrodes at multiple different frequencies,
wherein the co-located contactless circuitry is configured to detect and convert the current flow to impedance data and transmit the impedance data to the data collection system, and
wherein the impedance data is associated with a corrosion condition of the structure and/or the one or more coatings.

16. The sensing system in claim 15, wherein the sensing system is a walkup device for placement on a surface of the structure to obtain the impedance data is associated with a corrosion condition of the structure and/or the one or more coatings.

17. The sensing system in claim 15, wherein the data collection system is external and separated from the structure and any coatings on or over the structure, configured to wirelessly communicate with the sensing device and including a power source, control circuitry, and interface and communication circuitry,
  wherein the pair of contactless electrodes is configured to function as sensors when wirelessly activated by the data collection system to excite current flow between the electrodes at multiple different frequencies, and
  wherein the co-located contactless circuitry is configured to detect and convert the current flow to impedance data and wirelessly transmit the impedance data to the interface and communication circuitry of the data collection system over a radio frequency (RF) interface.

18. The sensing system of claim 17, wherein the data collection system is configured to transmit data and power via the interface and communication circuitry over the RF interface to the sensing device.

19. The sensing system of claim 15, further comprising:
  a data display system coupled to the data collection system and including a graphical user interface configured to communicate from or to a user information regarding the coating and/or corrosion condition of the structure.

20. The sensing system of claim 15, wherein the corrosion condition information includes an absolute or relative change in corrosion of the structure and/or the one or more coatings based on the impedance data associated with the pair of electrodes at the multiple different frequencies.

21. A method of sensing corrosion condition information, comprising:
  locating a pair of contactless electrodes of a sensing device on a coating on a surface of a structure or within or between one or more coatings on or over the surface of the structure;
  activating the pair of contactless electrodes to excite current flow between the electrodes at one or more frequencies;
  detecting and converting the current flow to impedance data; and
  providing the impedance data to a data collection system, wherein the impedance data is associated with a corrosion condition of the structure and/or the one or more coatings.

22. The method of claim 21, wherein the providing includes transmitting the impedance data to a data collection system over a radio frequency (RF) interface.

23. The method in claim 22, further comprising the data collection system transmitting data and power over an RF interface to the sensing device.

24. The method in claim 21, further comprising:
  communicating to a graphical user interface information regarding the coating and/or corrosion condition of the structure.

25. The method in claim 21, wherein the sensing device includes contactless circuitry co-located with the electrodes and having communications circuitry for wireless communication.

26. The sensor apparatus in claim 1, wherein the pair of contactless electrodes are placed on or within a coating on the surface of the structure or within or between one or more coatings on or over the surface of the structure, and wherein the pair of contactless electrodes do not require forced current or voltage through a direct electrical connection to the structure.

27. The sensing system in claim 15, wherein the pair of contactless electrodes do not require forced current or voltage through a direct electrical connection to the structure.

28. The method in claim 21, wherein the locating step includes placing the pair of contactless electrodes on or within a coating on the surface of the structure or within or between one or more coatings on or over the surface of the structure, and wherein the pair of contactless electrodes do not require forced current or voltage through a direct electrical connection to the structure.

* * * * *